US011155710B2

(12) United States Patent
Di Nicolo' et al.

(10) Patent No.: US 11,155,710 B2
(45) Date of Patent: Oct. 26, 2021

(54) COMPOSITION COMPRISING AROMATIC AND FLUORINATED POLYMERS AND USE THEREOF

(71) Applicant: SOLVAY SPECIALTY POLYMERS ITALY S.P.A., Bollate (IT)

(72) Inventors: Emanuele Di Nicolo', Gorla Minore (IT); Patrizia Maccone, Milan (IT); Silvia Rita Petricci, Bresso (IT); Pasquale Campanelli, Limbiate (IT)

(73) Assignee: SOLVAY SPECIALTY POLYMERS ITALY S.P.A., Bollate (IT)

( * ) Notice: Subject to any disclaimer, the term of this patent is extended or adjusted under 35 U.S.C. 154(b) by 226 days.

(21) Appl. No.: 16/324,063

(22) PCT Filed: Aug. 7, 2017

(86) PCT No.: PCT/EP2017/069901
§ 371 (c)(1),
(2) Date: Feb. 7, 2019

(87) PCT Pub. No.: WO2018/029133
PCT Pub. Date: Feb. 15, 2018

(65) Prior Publication Data
US 2019/0177539 A1   Jun. 13, 2019

(30) Foreign Application Priority Data
Aug. 9, 2016 (EP) .................................. 16183380

(51) Int. Cl.
| | |
|---|---|
| C08L 81/06 | (2006.01) |
| B01D 71/54 | (2006.01) |
| A61M 1/16 | (2006.01) |
| C08G 18/42 | (2006.01) |
| C08G 75/23 | (2006.01) |
| B01D 71/68 | (2006.01) |
| C08G 75/20 | (2016.01) |
| C08G 18/22 | (2006.01) |
| C08G 18/66 | (2006.01) |
| C08G 18/50 | (2006.01) |
| C08G 18/76 | (2006.01) |
| C08G 18/32 | (2006.01) |
| A61M 1/34 | (2006.01) |
| B01D 61/24 | (2006.01) |
| B01D 67/00 | (2006.01) |
| B01D 69/04 | (2006.01) |
| B01D 69/08 | (2006.01) |
| C08J 5/18 | (2006.01) |

(52) U.S. Cl.
CPC .......... *C08L 81/06* (2013.01); *A61M 1/1621* (2014.02); *A61M 1/3413* (2013.01); *B01D 61/243* (2013.01); *B01D 67/0013* (2013.01); *B01D 67/0016* (2013.01); *B01D 67/0097* (2013.01); *B01D 69/04* (2013.01); *B01D 69/08* (2013.01); *B01D 71/54* (2013.01); *B01D 71/68* (2013.01); *C08G 18/222* (2013.01); *C08G 18/3206* (2013.01); *C08G 18/4277* (2013.01); *C08G 18/5015* (2013.01); *C08G 18/6674* (2013.01); *C08G 18/7671* (2013.01); *C08G 75/20* (2013.01); *C08G 75/23* (2013.01); *C08J 5/18* (2013.01); *C08J 2381/06* (2013.01); *C08J 2475/08* (2013.01); *C08L 2203/12* (2013.01); *C08L 2203/16* (2013.01)

(58) Field of Classification Search
None
See application file for complete search history.

(56) References Cited

U.S. PATENT DOCUMENTS

| | | | |
|---|---|---|---|
| 5,332,798 A | 7/1994 | Ferreri et al. | |
| 2011/0009799 A1* | 1/2011 | Mullick | B01D 69/08 604/6.14 |
| 2016/0228824 A1* | 8/2016 | Hane | B01D 69/10 |

FOREIGN PATENT DOCUMENTS

| | | |
|---|---|---|
| WO | 2014072447 A1 | 5/2014 |
| WO | 2014072473 A2 | 5/2014 |

OTHER PUBLICATIONS

Khayet, M. et al., "Study on Surface Modification by Surface-Modifying Macromolecules and Its Applications in Membrane-Separation Processes", Journal of Applied Polymer Science, 89, 2003, pp. 2902-2916. (Year: 2003).*
Porter M.C., "Pore size determination", Handbook of industrial membrane technology, 1990, p. 70-78.
Smolders K. et al., "Terminology for Membrane Distillation", Desalination, 1989, vol. 72, issue 3, p. 249-262—Elsevier Science Publishers B.V., Amsterdam.

* cited by examiner

*Primary Examiner* — Jason M Greene
(74) *Attorney, Agent, or Firm* — Osha Bergman Watanabe & Burton LLP

(57) ABSTRACT

The present invention relates to a composition comprising at least one aromatic polymer and at least one fluorinated polymer, articles made from such compositions and uses thereof.

21 Claims, No Drawings

COMPOSITION COMPRISING AROMATIC AND FLUORINATED POLYMERS AND USE THEREOF

CROSS-REFERENCE TO RELATED PATENT APPLICATIONS

This application is a U.S. national stage entry under 35 U.S.C. § 371 of International Application No. PCT/EP2017/069901 filed Aug. 7, 2017, which claims priority to European patent application No. 16183380.1, filed on Aug. 9, 2016. The entire contents of these applications are explicitly incorporated herein by this reference.

TECHNICAL FIELD

The present invention relates to a composition comprising at least one aromatic polymer and at least one fluorinated polymer, articles made from such compositions and uses thereof.

BACKGROUND ART

Aromatic polymers are widely used in the preparation of microfiltration and ultrafiltration membranes due to their good mechanical strength and thermal stability.

Porous membranes are discrete, thin interface that moderate the permeation of chemical species in contact with them. The key property of porous membranes is their ability to control the permeation rate of chemical species through the membrane itself. This feature is exploited in many different applications like separation applications (water and gas) or drug delivery applications.

Polymeric membranes suitable for use as microfiltration and ultrafiltration typically control the permeation under a "sieve" mechanism since the passage of liquid or gas is mainly governed by a convective flux. Such polymeric membranes are mainly produced by phase inversion methods which can give raise to items with very large fraction of voids (porosity).

Porous polymeric membranes are mainly produced by phase-inversion methods, which provide items with a large fraction of voids (or in other words, with high porosity).

A homogeneous polymeric solution (also referred to as "dope solution") containing a polymer, a suitable solvent and/or a co-solvent and, optionally, one or more additives is typically processed by casting into a film and then brought to precipitation by contacting it with a non-solvent medium by the so-called Non-Solvent Induced Phase Separation (NIPS) process. The non-solvent medium is usually water or a mixture of water and surfactants, alcohols and/or the solvent itself.

Precipitation can also be obtained by decreasing the temperature of the polymeric solution by the so-called Thermal Induced Phase Separation (TIPS) process.

Alternatively, the precipitation may be induced by contacting the film processed by casting with air at a very high water vapour content by the so-called Vapour Induced Phase Separation (VIPS) process.

Still, the precipitation may be induced by evaporation of the solvent from the film processed by casting by the so-called Evaporation Induced Phase Separation (EIPS) process. Typically in this process an organic solvent with low boiling point (such as THF, acetone, MEK and the like) is used in admixture with water (the so called "non-solvent"). The polymer solution is first extruded and then precipitates due to the evaporation of the volatile solvent and the enrichment of the non-solvent.

The above processes can be used in combination and/or in sequence to provide membranes having specific morphology and performances. For example, EIPS process can be combined with the VIPS process and NIPS process in order to complete the coagulation process.

The EIPS process is known as "thermal coagulation process" when polyurethane polymers are used to manufacture porous membranes. In this case, the dope solution is prepared with a pre-polymer and as the membrane is formed, it is stabilized with a thermal post treatment to fix the porous structure and crosslink the pre-polymer.

SUMMARY OF INVENTION

The Applicant faced the problem to provide a composition for the manufacture of porous membranes exhibiting good mechanical properties and both hydro- and oleo-repellency.

In facing this technical problem, the Applicant found a composition suitable for the preparation of both porous and dense articles.

Thus, in a first aspect, the present invention relates to a composition [composition (C)] comprising:
  at least one aromatic polymer [polymer (A)], and
  at least one fluorinated polyurethane [F-TPU polymer], said F-TPU polymer comprising recurring units derived from:
optionally [monomer (a)] at least one diol selected from the group comprising poly-ether type diol, poly-ester type diol, polybutadien-diol and polycarbonate-diol;
[monomer (b)] at least one hydroxy-terminated (per)fluoropolyether polymer [PFPE polymer];
[monomer (c)] at least one aromatic, aliphatic or cycloaliphatic diisocyanate; and
[monomer (d)] at least one aliphatic, cycloaliphatic or aromatic diol having from 1 to 14 carbon atoms; and
  optionally at least one further ingredient.

In a second aspect, the present invention relates to a film comprising at least one layer obtained from of a composition [composition (C)] as defined above.

Advantageously, said film is a discrete, generally thin, dense layer.

In a third aspect, the present invention relates to a porous membrane comprising at least one layer obtained from of a composition [composition (C)] as defined above.

In a fourth aspect, the present invention relates to a process for manufacturing a film, said process comprising:
(i) providing a composition [composition (C)] as defined above;
(ii) processing the composition (C) provided in step (i) thereby providing a film.

The dense film of the invention is advantageously obtainable by the process as above defined.

In a fifth aspect, the present invention relates to a process for the manufacture of the porous membrane, said process comprising step (i) and step (ii) as defined above and step (iii) of processing the film provided in step (ii) thereby providing a porous membrane.

The porous membrane of the invention is advantageously obtained from the above defined process, in other words it is obtained from the dense film of the invention.

DESCRIPTION OF EMBODIMENTS

For the purposes of the present description:

the term "(per)fluoropolyether" is intended to indicate a "fully or partially fluorinated polyether";

the expression "(per)fluoropolyoxyalkylene chain" is intended to indicate a partially or fully fluorinated, straight or branched, polyoxyalkylene chain;

the use of parentheses before and after symbols or numbers identifying compounds, chemical formulae or parts of formulae has the mere purpose of better distinguishing those symbols or numbers from the rest of the text and hence said parentheses can also be omitted;

the term "membrane" is intended to indicate to a discrete, generally thin, interface that moderates the permeation of chemical species in contact with it, said membrane containing pores of finite dimensions;

the term "porous" is intended to indicate that the membrane of the invention contains pores distributed throughout its thickness;

the term "term" associated to "film" or "layer" is intended to indicate that the film or the layer does not contain pores distributed throughout its thickness or if pores are present, the gravimetric porosity is of less than 3%, more preferably less than 1% based on the total volume of the film;

the term "composition (C)" is intended to include both the liquid composition [composition ($C^L$)] and the solid composition [composition ($C^S$)], unless otherwise specified.

Preferably, the F-TPU polymer is a block copolymer, i.e. a polymer comprising blocks (also referred to as "segments"), each block comprising recurring units deriving from optional monomer (a), monomer (b), monomer (c) or monomer (d), as defined above.

Preferably, said F-TPU polymer has an average number molecular weight of from 30,000 to about 70,000 Da.

Preferably, said F-TPU polymer has a melting point ($T_m$) of from about 120° C. to about 240° C.

Preferably, said optional at least one monomer (a) has an average number molecular weight of from 500 to 4,000 Da, more preferably of from 1,000 to 4,000.

Preferably, said optional at least one monomer (a) is selected in the group comprising poly(ethylene)glycol, poly(propylene)glycol, poly(tetramethylen)glycol (PTMG), poly(1,4-butanediol)adipate, poly(ethandiol-1,4-butanediol) adipate, poly(1,6-hexandiol-neopentyl)glycol adipate, poly-caprolactone-diol (PCL) and polycarbonate-diol. Poly(tetramethylen)glycol, poly-caprolactone-diol and polycarbonate-diol being particularly preferred.

Preferably, said at least one monomer (b) is a hydroxy-terminated (per)fluoropolyether polymer [PFPE polymer], i.e. a polymer comprising a (per)fluoropolyoxyalkylene chain [chain ($R_{pf}$)] having two chain ends, wherein one or both chain ends terminates with at least one —OH group.

Preferably, at least one chain end of said chain ($R_{pf}$) terminates with a group of formula:

$$—CH_2(OCH_2CH_2)_t—OH \quad (I)$$

wherein
t is 0 or from 1 to 5.

More preferably, both chain ends of said chain ($R_{pf}$) terminate with a group of formula (I) as defined above.

Preferably, said chain ($R_{pf}$) is a chain of formula

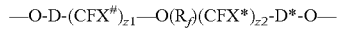

wherein z1 and z2, equal or different from each other, are equal to or higher than 1; $X^\#$ and $X^*$, equal or different from each other, are —F or —$CF_3$, provided that when z1 and/or z2 are higher than 1, $X^\#$ and $X^*$ are —F; D and $D^*$, equal or different from each other, are an alkylene chain comprising from 1 to 6 and even more preferably from 1 to 3 carbon atoms, said alkyl chain being optionally substituted with at least one perfluoroalkyl group comprising from 1 to 3 carbon atoms; ($R_f$) comprises, preferably consists of, repeating units $R°$, said repeating units being independently selected from the group consisting of:

(i) —CFXO—, wherein X is F or $CF_3$;

(ii) —CFXCFXO—, wherein X, equal or different at each occurrence, is F or $CF_3$, with the proviso that at least one of X is —F;

(iii) —$CF_2CF_2CW_2O$—, wherein each of W, equal or different from each other, are F, Cl, H;

(iv) —$CF_2CF_2CF_2CF_2O$—;

(v) —$(CF_2)_j$—CFZ—O— wherein j is an integer from 0 to 3 and Z is a group of general formula —O—$R_{(f-a)}$-T, wherein $R_{(f-a)}$ is a fluoropolyoxyalkene chain comprising a number of repeating units from 0 to 10, said recurring units being chosen among the following: —CFXO—, —$CF_2CFXO$—, —$CF_2CF_2CF_2O$—, —$CF_2CF_2CF_2CF_2O$—, with each of each of X being independently F or $CF_3$ and T being a $C_1$-$C_3$ perfluoroalkyl group.

More preferably, chain ($R_f$) is selected from the following formulae ($R_f$-a) to ($R_f$-c):

($R_f$-a)      —$(CF_2O)_n(CF_2CF_2O)_m(CF_2CF_2CF_2O)_p$ $(CF_2CF_2CF_2CF_2O)_q$— wherein m, n, p, q are 0 or integers selected in such a way as chain $R_f$ meets the above number average molecular weight requirement, with the proviso that if, p and q are simultaneously 0, n is not 0; when m is other than 0, the m/n ratio is preferably between 0.1 and 20; when (m+n) is other than 0, (p+q)/(m+n) is preferably between 0 and 0.2;

($R_f$-b)   —$(CF_2CF(CF_3)O)_a(CF_2CF_2O)_b(CF_2O)_c(CF(CF_3) O)_d$ — wherein a, b, c, d are 0 or integers selected in such a way as chain $R_f$ meets the above number average molecular weight requirement; with the proviso that, at least one of a, c and d is not 0; when b is other than 0, a/b is preferably between 0.1 and 10; when (a+b) is different from 0 (c+d)/(a+b) preferably is between 0.01 and 0.5, more preferably between 0.01 and 0.2;

($R_f$-c)  —$(CF_2CF(CF_3)O)_e(CF_2O)_f(CF(CF_3)O)_g$— wherein e, f, g are 0 or integers selected in such a way as chain $R_f$ meets the above number average molecular weight requirement; when e is other than 0, (f+g)/e is preferably between 0.01 and 0.5, more preferably between 0.01 and 0.2.

PFPE polymers wherein chain ($R_f$) complies with formula ($R_f$-a) as defined above, wherein p and q are 0, are particularly preferred in the present invention.

In a preferred embodiment, said PFPE polymer complies with the following formula (PFPE-I):

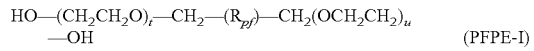

wherein
t and u are, each independently, 0 or from 1 to 5; and $R_{pf}$ is as defined above.

Preferably, said PFPE polymer has an average number molecular weight of from 400 to 10,000 Da, more preferably from 1,000 to 5,000.

In a preferred embodiment, the molar ratio between monomers (a) and monomers (b) is from 2 to 20, more preferably from 2 to 10.

In a preferred embodiment, the amount of monomers (b) is such that the F-TPU polymer comprises from 1 to 80 wt. % of fluorine, preferably from 1 to 70 wt. % based on the weight of the F-TPU polymer.

Preferably, said at least one monomer (c) has a number molecular weight of 500 Da or lower, preferably from 10 to 500 Da.

Preferably, said at least one monomer (c) is selected in the group comprising, preferably consisting of, 4,4'-methylene-diphenylene-diisocyanate (MDI), 1,6-hexan-diisocyanate (HDI), 2,4-toluene-diisocyanate, 2,6-toluene-diisocyanate, xylilen-diisocyanate, naphthalene-diisocyanate, paraphe-nylen-diisocyanate, hexamaethylen-diisocyanate, iso-phorone-diisocyanate, 4,4'-dicyclohexyl-methane-diisocyanate and cyclohexyl-1,4-diisocyanate.

MDI and HDI being particularly preferred.

Preferably, said at least one monomer (d) is selected in the group comprising, preferably consisting of, ethylene-glycol, 1,4-butanediol (BDO), 1,6-hexane diol (HDO), N,N-dietha-nolamine and N,N-diisopropanolaniline. BDO and HDO being particularly preferred.

In a preferred embodiment, the sum of blocks deriving from monomers (c) and (d) is from 10 to 60 wt. % based on the total weight of the F-TPU polymer.

Those skilled in the art would readily understand that blocks comprising recurring units derived from monomer (b) and monomer (a) when present are rubber-like blocks, while blocks comprising recurring units derived from monomers (c) and (d) are hard blocks.

In a preferred embodiment, at least 80% of the blocks comprising recurring units derived from said monomers (b) [blocks B] are linked, at least one of their ends, to a block comprising recurring units derived from monomers (a) [blocks A] through a block comprising recurring units derived from monomers (c) [blocks C].

In other words, at least 80% of blocks B are contained in a sequence of the following type: -[A-C—B-C]-.

Advantageously, the F-TPU polymer can be prepared according to methods known in the art, such as for example extrusion, injection moulding, casting of a solution of the monomers defined above or following the procedures disclosed in U.S. Pat. No. 5,332,798 (AUSIMONT S.P.A.).

The polymer (A) is typically selected from the group consisting of poly(arylene sulfide) polymers [polymers (PAS)] and aromatic sulfone polymers [polymers (SP)].

For the purpose of the present invention, the term "poly (arylene sulfide) polymer [polymer (PAS)]" is intended to denote any polymer comprising recurring units wherein more than 50% by moles of said recurring units are recurring units ($R_{PAS}$) of formula:

—(Ar-S)— wherein Ar denotes an aromatic moiety comprising at least one aromatic mono- or poly-nuclear cycle, such as a phenylene or a naphthylene group, which is linked by each of its two ends to two sulfur atoms forming sulfide groups via a direct C—S linkage.

In recurring units ($R_{PAS}$), the aromatic moiety Ar may be substituted by one or more substituent groups, including but not limited to halogen atoms, $C_1$-$C_{12}$ alkyl groups, $C_7$-$C_{24}$ alkylaryl groups, $C_7$-$C_{24}$ aralkyl groups, $C_6$-$C_{24}$ arylene groups, $C_1$-$C_{12}$ alkoxy groups, and $C_6$-$C_{18}$ aryloxy groups, and substituted or unsubstituted arylene sulfide groups, the arylene groups of which are also linked by each of their two ends to two sulfur atoms forming sulfide groups via a direct C—S linkage thereby creating branched or cross-linked polymer chains.

The polymer (PAS) preferably comprises more than 70% by moles, more preferably more than 80% by moles, still more preferably more than 90% by moles of recurring units ($R_{PAS}$).

Most preferably, the polymer (PAS) contains no recurring units other than recurring units ($R_{PAS}$).

In recurring units ($R_{PAS}$), the aromatic moiety Ar is preferably selected from the group consisting of those of formulae (X-A) to (X-K) here below:

(X-A)

(X-B)

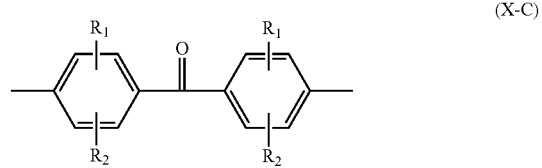
(X-C)

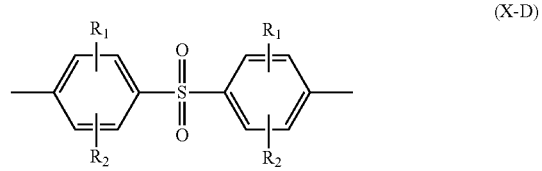
(X-D)

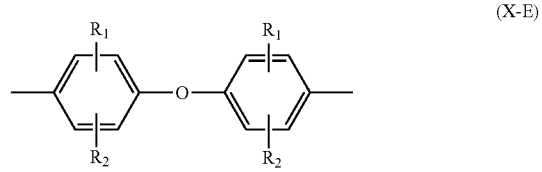
(X-E)

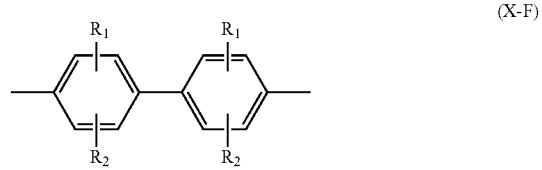
(X-F)

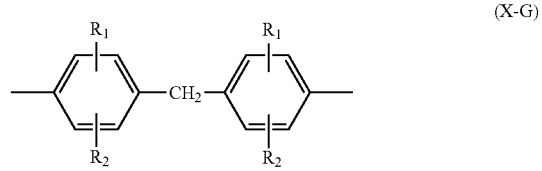
(X-G)

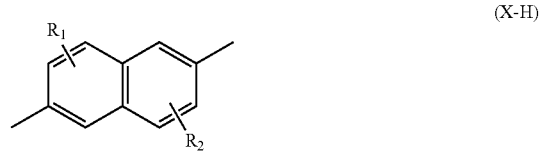
(X-H)

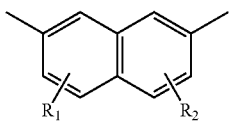

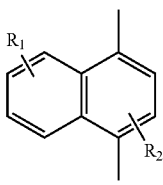

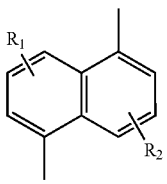

wherein $R_1$ and $R_2$, equal to or different from each other, are selected from the group consisting of hydrogen atoms, halogen atoms, $C_1$-$C_{12}$ alkyl groups, $C_7$-$C_{24}$ alkylaryl groups, $C_7$-$C_{24}$ aralkyl groups, $C_6$-$C_{24}$ arylene groups, $C_1$-$C_{12}$ alkoxy groups, and $C_6$-$C_{18}$ aryloxy groups, and substituted or unsubstituted arylene sulfide groups, the arylene groups of which are also linked by each of their two ends to two sulfur atoms forming sulfide groups via a direct C—S linkage thereby creating branched or cross-linked polymer chains.

The polymer (PAS) may be a homopolymer or a copolymer such as a random copolymer or a block copolymer.

The polymer (PAS) typically comprises one or more branched or cross-linked recurring units selected from the group consisting of those of formulae (X-L) to (X-N) here below:

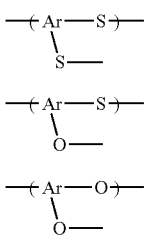

The polymer (PAS) is preferably a poly(phenylene sulfide) polymer [polymer (PPS)]. For the purpose of the present invention, the term "poly(phenylene sulfide) polymer [polymer (PPS)]" is intended to denote any polymer comprising recurring units wherein more than 50% by moles of said recurring units are p-phenylene sulfide recurring units ($R_{PPS}$) of formula:

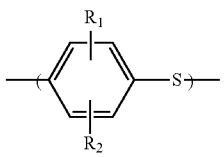

wherein the p-phenylene group is linked by each of its two ends to two sulfur atoms forming sulfide groups via a direct C—S linkage, wherein $R_1$ and $R_2$, equal to or different from each other, are selected from the group consisting of hydrogen atoms, halogen atoms, $C_1$-$C_{12}$ alkyl groups, $C_7$-$C_{24}$ alkylaryl groups, $C_7$-$C_{24}$ aralkyl groups, $C_6$-$C_{24}$ arylene groups, $C_1$-$C_{12}$ alkoxy groups, and $C_6$-$C_{18}$ aryloxy groups, and substituted or unsubstituted arylene sulfide groups, the arylene groups of which are also linked by each of their two ends to two sulfur atoms forming sulfide groups via a direct C—S linkage thereby creating branched or cross-linked polymer chains.

Non-limiting examples of polymers (PPS) suitable for the invention include those commercially available under the trademark names RYTON® from Solvay Specialty Polymers USA L.L.C., FORTRON® from Fortron Industries and UPEC® from GE Plastics.

For the purpose of the invention, the term "aromatic sulfone polymer [polymer (SP)]" is intended to denote any polymer comprising recurring units wherein more than 50% by moles of the recurring units of said polymer (SP) are connected by ether linkages in the main chain and comprise at least one group of formula -Ar-$SO_2$-Ar'- [recurring units ($R_{SP}$)], wherein Ar and Ar', equal to or different from each other, are aromatic groups.

In a first preferred embodiment of the invention, the recurring units ($R_{SP}$) of the polymer (SP) are preferably recurring units ($R_{SP-1}$) of formula:

$$\text{-Ar}^1\text{-(T'-Ar}^2)_n\text{-O—Ar}^3\text{-SO}_2\text{-[Ar}^4\text{-(T-Ar}^2)_n\text{-SO}_2]_m\text{-Ar}^5\text{-O—} \quad (R_{SP-1})$$

wherein:
  $Ar^1$, $Ar^2$, $Ar^3$, $Ar^4$, and $Ar^5$, equal to or different from each other and at each occurrence, are independently aromatic mono- or polynuclear groups;
  T and T', equal to or different from each other and at each occurrence, is independently a bond or a divalent group optionally comprising one or more than one heteroatoms; preferably T' is selected from the group consisting of a bond, —$CH_2$—, —C(O)—, —C($CH_3$)$_2$—, —C($CF_3$)$_2$—, —C(=$CCl_2$)—, —$SO_2$—, —C($CH_3$)($CH_2CH_2COOH$)—, and a group of formula:

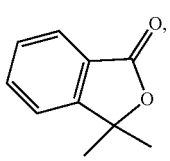

and
preferably T is selected from the group consisting of a bond, —$CH_2$—, —C(O)—, —C($CH_3$)$_2$—, —C($CF_3$)$_2$—, —C(=$CCl_2$)—, —C($CH_3$)($CH_2CH_2COOH$)—, and a group of formula:

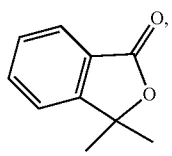

and n and m, equal to or different from each other, are independently zero or an integer of 1 to 5.

Non limiting examples of polymers (SP) according to this first preferred embodiment of the invention include poly(phenylene sulfone) polymers [polymers (PPSU)], poly(sulfone) polymers [polymers (PSU)] and poly(ether sulfone) polymers [polymers (PESU)].

For the purpose of the invention, the term "poly(phenylene sulfone) polymer [polymer (PPSU)]" is intended to denote any polymer comprising recurring units wherein more than 50% by moles of the recurring units ($R_{SP-1}$) of said polymer (PPSU) are recurring units ($R_{PPSU}$) of formula (K-A):

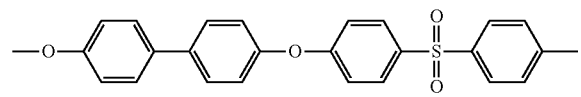

(K-A)

In a preferred embodiment of the present invention, more than 75% by moles, preferably more than 90% by moles, more preferably more than 99% by moles, even more preferably substantially all the recurring units ($R_{SP-1}$) of the polymer (PPSU) are recurring units ($R_{PPSU}$) of formula (K-A), chain defects or minor amounts of other recurring units might be present, being understood that these latter do not substantially modify the properties of the polymer (PPSU).

The polymer (PPSU) polymer may be notably a homopolymer or a copolymer such as a random copolymer or a block copolymer. When the (PPSU) polymer is a copolymer, its recurring units are advantageously a mix of recurring units ($R_{PPSU}$) of formula (K-A) and of recurring units ($R_{PPSU}$), different from recurring units ($R_{PPSU}$), such as recurring units of formula (K-B), (K-C) or (K-D):

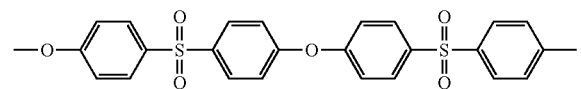

(K-B)

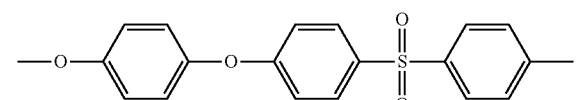

(K-C)

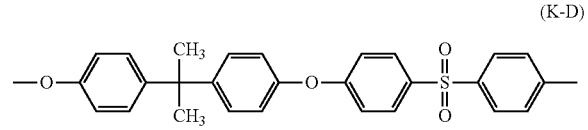

(K-D)

and mixtures thereof.

The polymer (PPSU) can also be a blend of a homopolymer and a copolymer as defined above.

Non-limiting examples of polymers (PPSU) suitable for the invention include those commercially available under the trademark names RADEL® R PPSU from Solvay Specialty Polymers USA L.L.C.

For the purpose of the present invention, the term "poly(sulfone) polymer [polymer (PSU)]" is intended to denote an aromatic sulfone polymer wherein at least 50% by moles, preferably at least 60% by moles, more preferably at least 70% by moles, even more preferably at least 80% by moles and most preferably at least 90% by moles of the recurring units ($R_{SP-1}$) of said polymer (PSU) are recurring units ($R_{PSU}$) of formula:

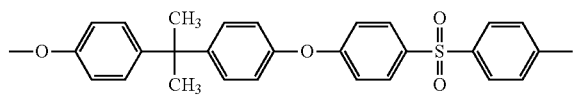

Non-limiting examples of polymers (PSU) suitable for the invention include those commercially available under the trademark name UDEL® PSU from Solvay Specialty Polymers USA L.L.C.

For the purpose of the present invention, the term "poly(ether sulfone) polymer [polymer (PESU)]" is intended to denote any polymer wherein more than 50% by moles of the recurring units ($R_{SP-1}$) of said polymer (PESU) are recurring units ($R_{PESU}$) of formula:

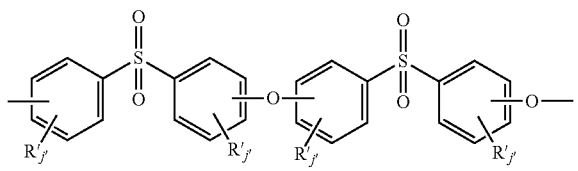

wherein each of R', equal to or different from each other, is selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium, and each of j', equal to or different from each other and at each occurrence, is independently zero or is an integer from 0 to 4.

Preferred recurring units ($R_{PESU}$) are those complying with formula (I), shown below:

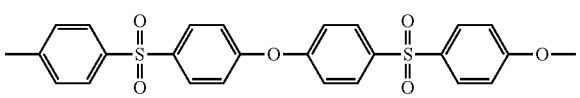

The polymer (PESU) may be notably a homopolymer or a copolymer such as a random or a block copolymer.

When the polymer (PESU) is a copolymer, its recurring units are advantageously a mix of recurring units ($R_{PESU}$), as defined above, and of recurring units ($R_{PESU}^*$). The recurring units ($R_{PESU}^*$) are typically selected from the group consisting of those of formulae (II), (III) and (IV) here below:

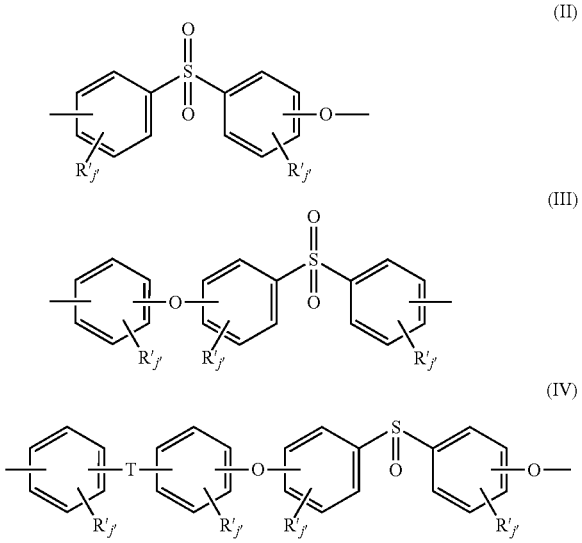

(II)

(III)

(IV)

wherein:
each of R', equal to or different from each other, is selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium;

each of i', equal to or different from each other and at each occurrence, is independently zero or is an integer from 0 to 4;

each of T, equal to or different from each other, is selected from the group consisting of a bond, —CH$_2$—; —O—; —S—; —C(O)—; —C(CH$_3$)$_2$—; —C(CF$_3$)$_2$—; —C(=CCl$_2$)—; —C(CH$_3$)(CH$_2$CH$_2$COOH)—; —N=N—; —R$^a$C=CR$^b$—; where each R$^a$ and R$^b$, independently of one another, is a hydrogen or a C$_1$-C$_{12}$-alkyl, C$_1$-C$_{12}$-alkoxy, or C$_6$-C$_{18}$-aryl group; —(CH$_2$)$_q$— and —(CF$_2$)$_q$— wherein q is and integer from 1 to 6, or an aliphatic divalent group, linear or branched, of up to 6 carbon atoms; and mixtures thereof.

Specific recurring units (R$_{PESU}$*) are typically selected from the group consisting of those of formula (A), (B) and (C) here below:

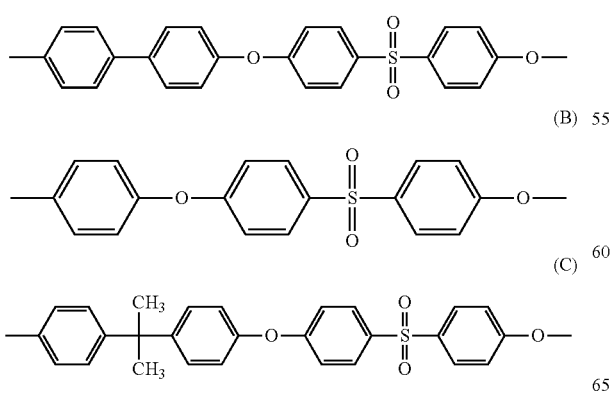

(A)

(B)

(C)

and mixtures thereof.

The polymer (PESU) may be a blend of the previously cited homopolymer and copolymer.

Preferably more than 75% by moles, preferably more than 85% by moles, preferably more than 95% by moles, preferably more than 99% by moles of the recurring units of the polymer (PESU) are recurring units (R$_{PESU}$), as defined above.

Most preferably, all the recurring units of the polymer (PESU) are recurring units (R$_{PESU}$), as defined above, chain defects, or very minor amounts of other units might be present, being understood that these latter do not substantially modify the properties.

Non-limiting examples of polymers (PESU) suitable for the invention include, for instance, those described in WO 2014/072447 (SOLVAY SPECIALTY POLYMERS ITALY S.P.A.) 15 May 2014.

Non-limiting examples of polymers (PESU) suitable for the invention include those commercially available under the trademark name VERADEL® PESU from Solvay Specialty Polymers USA L.L.C.

In a second preferred embodiment of the invention, the recurring units (R$_{SP}$) of the polymer (SP) are preferably recurring units (R$_{SP-2}$) of formula:

(R$_{SP-2}$)

wherein each of Ar*$^1$, Ar*$^2$, Ar*$^3$ and Ar*$^4$, equal to or different from each other at each occurrence, is an aromatic moiety;

n* and m*, equal to or different from each other, are independently zero or an integer of 1 to 5;

T* is a bond or a divalent group optionally comprising one or more than one heteroatom; preferably T* is selected from the group consisting of a bond, —CH$_2$—, —C(CH$_3$)$_2$—, —C(CF$_3$)$_2$—, —C(=CCl$_2$)—, —C(CH$_3$)(CH$_2$CH$_2$COOH)—, and a group of formula:

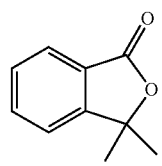

and

E is a 1,4:3,6-dianhydrohexitol sugar diol unit selected from one or more of formulae (E-1) to (E-3):

(E-1)

(E-2)

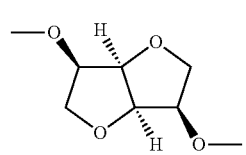

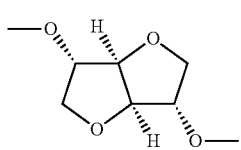
(E-3)

Preferred aromatic moieties Ar*¹-Ar*⁴ have the following structures:

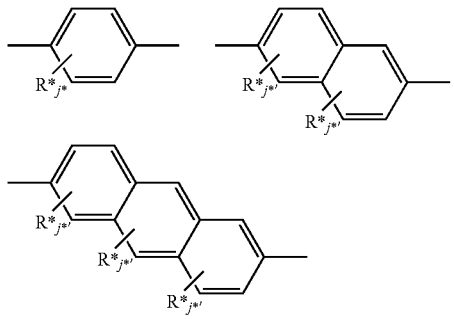

wherein:
each R* is independently selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium; and j* is zero or an integer of 1 to 4 and j*' is zero or an integer of 1 to 3.

Polymers (SP) according to this second preferred embodiment of the invention can be manufactured by reaction of at least one 1,4:3,6-dianhydrohexitol [diol (AA)] as defined above with at least one dihaloaryl compound [herein after dihalo (BB)] of formula (S):

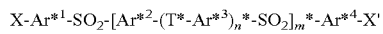

wherein:
X and X', equal to or different from each other, are halogens selected from F, Cl, Br, I; preferably Cl or F; and Ar*¹, Ar*², Ar*³, Ar*⁴, T*, n* and m* are as defined above.

A convenient method for manufacturing polymers (SP) according to this second preferred embodiment of the invention is disclosed in WO 2014/072473 (SOLVAY SPECIALTY POLYMERS ITALY S.P.A.) 15 May 2014, incorporated by reference herein.

Non limiting examples of polymers (SP) according to this second preferred embodiment of the invention include poly (isosorbide) polymers [polymers (PSI)].

For the purpose of the present invention, the term "poly (isosorbide) polymer [polymer (PSI)]" is intended to denote any polymer comprising recurring units wherein more than 30% by moles of the recurring units ($R_{SP\text{-}2}$) of said polymer are recurring units ($R_{PSI}$) independently selected from one or more of those of formulae ($R_{PSI}$-1) and ($R_{PSI}$-2):

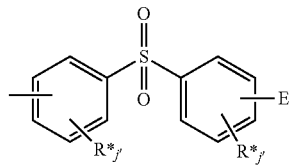

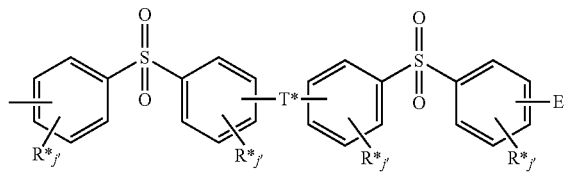

wherein:
each of R*, equal to or different from each other, is as defined above;

j* is as defined above;

T* is as defined above and is preferably selected from the group consisting of a bond, —$CH_2$—, —C(O)—, —$C(CH_3)_2$—, —$C(CF_3)_2$—, —C(=$CCl_2$)—, —$C(CH_3)(CH_2CH_2COOH)$—, —$SO_2$—, phenylene and a group of formula:

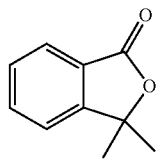

and

E is a 1,4:3,6-dianhydrohexitol sugar diol unit of formulae (E-1) [hereinafter also referred to as isosorbide unit (E-1)].

Recurring units ($R_{PSI}$-1) and ($R_{PSI}$-2) can be each present alone or in admixture.

More preferred polymers (PSI) are those comprising recurring units of formulae ($R_{PSI}$-1) and ($R_{PSI}$-2), wherein E is a 1,4:3,6-dianhydrohexitol sugar diol unit of formula (E-1), optionally in combination with one or more ($R_{PSI}$-1) and ($R_{PSI}$-2) units, wherein E is a 1,4:3,6-dianhydrohexitol sugar diol unit of formula (E-2) and/or (E-3) [hereinafter also referred to as isomannide and isoidide units (E-2) and (E-3), respectively].

Most preferred polymers (PSI) are those comprising recurring units of formula ($R_{PSI}$-1), wherein E is an isosorbide unit (E-1), optionally in combination with recurring units ($R_{PSI}$-1), wherein E is an isomannide unit of formula (E-2) and/or an isoidide unit of formula (E-3).

In recurring units ($R_{PSI}$-1) and ($R_{PSI}$-2), the respective phenylene moieties may independently have 1,2-, 1,4- or 1,3-linkages to the other moieties different from R* in the recurring units. Preferably, said phenylene moieties have 1,3- or 1,4-linkages, more preferably they have 1,4-linkages. Still, in recurring units ($R_{PSI}$-1) and ($R_{PSI}$-2), j* is at each occurrence zero, that is to say that the phenylene moieties have no other substituents than those enabling linkage in the main chain of the polymer.

Polymers (PSI) may optionally further comprise recurring units selected from one or more of:

recurring units ($R_{A'A'}$), deriving from the incorporation of at least one dihydroxyl compound [diol (A'A')] different from diol (AA);

recurring units ($R_{B'B'}$), deriving from the incorporation of at least one dihaloaryl compound [dihalo (B'B')] different from dihalo (BB);

recurring units ($R_{A'B'}$), deriving from the incorporation of at least one hydroxyl-halo compound [hydro-halo (A'B')];

recurring units ($R_e$) of formula (S1):

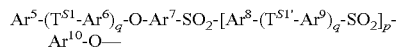

Ar$^5$-(T$^{S1}$-Ar$^6$)$_q$-O-Ar$^7$-SO$_2$-[Ar$^8$-(T$^{S1'}$-Ar$^9$)$_q$-SO$_2$]$_p$-Ar$^{10}$-O— wherein:

Ar$^5$, Ar$^6$, Ar$^7$, Ar$^8$ and Ar$^9$, equal to or different from each other and at each occurrence, are independently an aromatic moiety;

T$^{S1}$ and T$^{S1'}$, equal to or different from each other at each occurrence, are independently a bond or a divalent group optionally comprising one or more than one heteroatom; preferably T$^{s1}$ and T$^{s1'}$ are selected from the group consisting of a bond, —CH$_2$—, —C(O)—, —C(CH$_3$)$_2$—, —C(CF$_3$)$_2$—, —C(=CCl$_2$)—, —C(CH$_3$)(CH$_2$CH$_2$COOH)—, —SO$_2$—, and a group of formula:

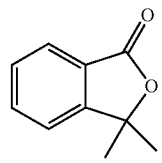

q and p, equal to or different from each other, are independently zero or an integer of 1 to 5.

Recurring units ($R_c$) can be notably selected from the group consisting of those of formulae (S1-A) to (S1-D) here below:

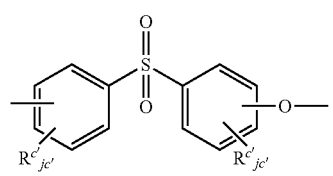
(S1-A)

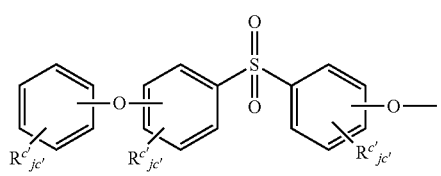
(S1-B)

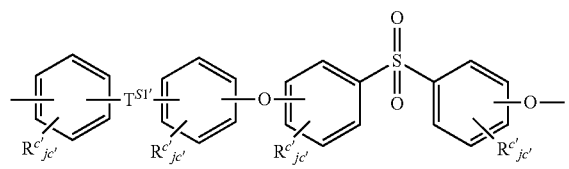
(S1-C)

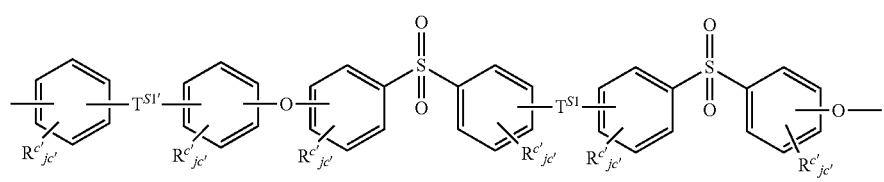
(S1-D)

wherein:
each of $R^{c'}$, equal to or different from each other, is selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium;

$j^{c'}$ is zero or is an integer from 0 to 4;

$T^{S1}$ and $T^{S1'}$ are as defined above.

In recurring units of any of formulae (S1-C) to (S1-D), the respective phenylene moieties may independently have 1,2-, 1,4- or 1,3-linkages to the other moieties different from R' in the recurring unit. Preferably, said phenylene moieties have 1,3- or 1,4-linkages, more preferably they have 1,4-linkages. Still, in recurring units of any of formulae (S1-C) to (S1-D), $j^{c'}$ is at each occurrence zero, that is to say that the phenylene moieties have no other substituents than those enabling linkage in the main chain of the polymer.

Polymers (PSI) typically comprise recurring units of formula ($R_{PSI}$) as defined above in an amount of at least 30% by moles, preferably 35% by moles, more preferably 40% by moles, even more preferably at least 50% by moles, with respect to all recurring units of polymers (PSI).

According to certain preferred embodiments, more than 70% by moles, and more preferably more than 85% by moles of the recurring units of the polymers (PSI) are recurring units ($R_{PSI}$), as defined above, the complement to 100% moles being generally recurring units ($R_c$) as defined above.

Methods for the manufacture of polymers (PSI) further comprising recurring units in addition to units ($R_{PSI}$) are also disclosed in the aforementioned WO 2014/072473 (SOLVAY SPECIALTY POLYMERS ITALY S.P.A.) May 15, 2014.

Preferably, the polymers (PSI) consist only of recurring units ($R_{PSI}$) as defined above, preferably recurring units ($R_{PSI}$-1), wherein (E) is an isosorbide unit of formula (E-1) and wherein the phenylene units have 1,4-linkages.

The polymers (PSI) have in general a weight average molecular weight of at least 20,000, preferably at least 30,000, more preferably at least 40,000. The weight average molecular weight ($M_w$) and the number average molecular weight ($M_n$) can be estimated by gel-permeation chromatography (GPC) using ASTM D5296 calibrated with polystyrene standards.

The weight average molecular weight ($M_w$) is:

$$M_w = \frac{\sum M_i^2 \cdot N_i}{\sum M_i \cdot N_i}$$

The number average molecular weight ($M_n$) is:

$$M_n = \frac{\sum M_i \cdot N_i}{\sum N_i}$$

The polydispersity index (PDI) is hereby expressed as the ratio of weight average molecular weight ($M_w$) to number average molecular weight (Me).

Polymers (PSI) generally have a polydispersity index of less than 2.5, preferably of less than 2.4, more preferably of less than 2.2. This relatively narrow molecular weight distribution is representative of an ensemble of molecular chains with similar molecular weights and substantially free from oligomeric fractions, which might have a detrimental effect on polymer properties.

Polymers (PSI) advantageously possess a glass transition temperature of at least 200° C., preferably 210° C., more preferably at least 220° C. Glass transition temperature (Tg) is generally determined by differential scanning calorimetry (DSC) according to ASTM D 3418 standard procedure.

The film according to the present invention is advantageously a dense film.

Membranes containing pores homogeneously distributed throughout their thickness are generally known as symmetric (or isotropic) membranes; membranes containing pores which are heterogeneously distributed throughout their thickness are generally known as asymmetric (or anisotropic) membranes.

The porous membrane according to the present invention may be either a symmetric membrane or an asymmetric membrane.

The asymmetric porous membrane typically consists of one or more layers containing pores which are heterogeneously distributed throughout their thickness.

The asymmetric porous membrane typically comprises an outer layer containing pores having an average pore diameter smaller than the average pore diameter of the pores in one or more inner layers.

The porous membrane of the invention preferably has an average pore diameter of at least 0.001 μm, more preferably of at least 0.005 μm, and even more preferably of at least 0.01 μm. The porous membrane of the invention preferably has an average pore diameter of at most 50 μm, more preferably of at most 20 μm and even more preferably of at most 15 μm.

Suitable techniques for the determination of the average pore diameter in the porous membranes of the invention are described for instance in Handbook of Industrial Membrane Technology. Edited by PORTER. Mark C. Noyes Publications, 1990. p. 70-78. Average pore diameter is preferably determined by scanning electron microscopy (SEM).

The porous membrane of the invention typically has a gravimetric porosity comprised between 5% and 90%, preferably between 10% and 85% by volume, more preferably between 30% and 90%, based on the total volume of the membrane.

For the purpose of the present invention, the term "gravimetric porosity" is intended to denote the fraction of voids over the total volume of the porous membrane.

Suitable techniques for the determination of the gravimetric porosity in the porous membranes of the invention are described for instance in SMOLDERS K., et al. Terminology for membrane distillation. Desalination. 1989, vol. 72, p. 249-262.

The porous membrane of the invention may be either a self-standing porous membrane or a porous membrane supported onto a substrate.

A porous membrane supported onto a substrate is typically obtainable by coating said substrate with said porous membrane or by impregnating or dipping said substrate with said composition (C) as defined above.

The porous membrane of the invention may further comprise at least one substrate layer. The substrate layer may be partially or fully interpenetrated by the porous membrane of the invention.

The nature of the substrate is not particularly limited. The substrate generally consists of materials having a minimal influence on the selectivity of the porous membrane. The substrate layer preferably consists of non-woven materials, glass fibers and/or polymeric material such as for example polypropylene, polyethylene and polyethyleneterephthalate.

The porous membrane of the invention may be a porous composite membrane comprising:
- at least one substrate layer, preferably a non-woven substrate,
- at least one top layer, and
- between said at least one substrate layer and said at least one top layer, at least one layer consisting of a composition (C) as defined above.

Typical examples of such porous composite membranes are the so called Thin Film Composite (TFC) structures which are typically used in reverse osmosis or nanofiltration applications.

Non limiting examples of top layers suitable for use in the porous composite membrane of the invention include those made of polymers selected from the group consisting of polyamides, polyimides, polyacrylonitriles, polybenzimidazoles, cellulose acetates and polyolefins.

Under step (i) of the process for manufacturing the film according to the invention, composition (C) is typically manufactured by any conventional techniques.

Under step (ii) of the process for manufacturing the film according to the invention, conventional techniques can be used for processing the composition (C) thereby providing a film.

The film provided under step (ii) can be further processed in order to provide a porous membrane.

Depending on the final form of the membrane, the film may be either flat, when flat membranes are required, or tubular in shape, when tubular or hollow fiber membranes are required.

According to a first embodiment of the invention, the process for manufacturing the film or the porous membrane according to the present invention is carried out in liquid phase.

The process according to this first embodiment of the invention typically comprises:
(iˆ) providing a liquid composition [composition ($C^L$)] comprising:
- at least one polymer (A) as defined above,
- at least one F-TPU polymer as defined above, and
- a liquid medium comprising at least one organic solvent [medium (L)];

(iiˆ) processing composition ($C^L$) provided in step (iˆ) thereby providing a film; and optionally,
(iiiˆ) precipitating the film provided in step (iiˆ) thereby providing a porous membrane.

The composition ($C^L$) is advantageously a homogeneous solution comprising:
- at least one polymer (A) as defined above,
- at least one F-TPU polymer as defined above, and
- a liquid medium comprising at least one organic solvent [medium (L)].

The term "solvent" is used herein in its usual meaning, that is it indicates a substance capable of dissolving another substance (solute) to form an uniformly dispersed mixture at the molecular level. In the case of a polymeric solute, it is common practice to refer to a solution of the polymer in a solvent when the resulting mixture is transparent and no phase separation is visible in the system. Phase separation is taken to be the point, often referred to as "cloud point", at which the solution becomes turbid or cloudy due to the formation of polymer aggregates.

The medium (L) typically comprises at least one organic solvent selected from the group comprising:

aliphatic hydrocarbons including, more particularly, the paraffins such as, in particular, pentane, hexane, heptane, octane, nonane, decane, undecane, dodecane or cyclohexane, and naphthalene and aromatic hydrocarbons and more particularly aromatic hydrocarbons such as, in particular, benzene, toluene, xylenes, cumene, petroleum fractions composed of a mixture of alkylbenzenes;

aliphatic or aromatic halogenated hydrocarbons including more particularly, perchlorinated hydrocarbons such as, in particular, tetrachloroethylene, hexachloroethane;

partially chlorinated hydrocarbons such as dichloromethane, chloroform, 1,2-dichloroethane, 1,1,1-trichloroethane, 1,1,2,2-tetrachloroethane, pentachloroethane, trichloroethylene, 1-chlorobutane, 1,2-dichlorobutane, monochlorobenzene, 1,2-dichlorobenzene, 1,3-dichlorobenzene, 1,4-dichlorobenzene, 1,2,4-trichlorobenzene or mixture of different chlorobenzenes;

aliphatic, cycloaliphatic or aromatic ether oxides, more particularly, diethyl oxide, dipropyl oxide, diisopropyl oxide, dibutyl oxide, methylterbutyl ether, dipentyl oxide, diisopentyl oxide, ethylene glycol dimethyl ether, ethylene glycol diethyl ether, ethylene glycol dibutyl ether benzyl oxide; dioxane, tetrahydrofuran (THF);

dimethylsulfoxide (DMSO);

glycol ethers such as ethylene glycol monomethyl ether, ethylene glycol monoethyl ether, ethylene glycol monopropyl ether, ethylene glycol monoisopropyl ether, ethylene glycol monobutyl ether, ethylene glycol monophenyl ether, ethylene glycol monobenzyl ether, diethylene glycol monomethyl ether, diethylene glycol monoethyl ether, diethylene glycol mono-n-butyl ether;

glycol ether esters such as ethylene glycol methyl ether acetate, ethylene glycol monoethyl ether acetate, ethylene glycol monobutyl ether acetate;

alcohols, including polyhydric alcohols, such as methyl alcohol, ethyl alcohol, diacetone alcohol, ethylene glycol;

ketones such as acetone, methylethylketone, methylisobutyl ketone, diisobutylketone, cyclohexanone, isophorone;

linear or cyclic esters such as isopropyl acetate, n-butyl acetate, methyl acetoacetate, dimethyl phthalate, γ-butyrolactone;

linear or cyclic carboxamides such as N,N-dimethylacetamide (DMAc), N,N-diethylacetamide, dimethylformamide (DMF), diethylformamide or N-methyl-2-pyrrolidone (NMP);

organic carbonates for example dimethyl carbonate, diethyl carbonate, dipropyl carbonate, dibutyl carbonate, ethylmethyl carbonate, ethylene carbonate, vinylene carbonate;

phosphoric esters such as trimethyl phosphate, triethyl phosphate (TEP);

ureas such as tetramethylurea, tetraethylurea;

methyl-5-dimethylamino-2-methyl-5-oxopentanoate (commercially available under the tradename Rhodialsov Polarclean®).

The following are particularly preferred: N-methyl-pyrrolidone (NMP), dimethyl acetamide (DMAc), dimethylformamide (DMF), dimethylsulfoxide (DMSO), tetrahydrofuran (THF), methyl-5-dimethylamino-2-methyl-5-oxopentanoate (commercially available under the tradename Rhodialsov Polarclean®) and triethylphosphate (TEP).

The medium (L) preferably comprises at least 40 wt. %, more preferably at least 50 wt. % based on the total weight of said medium (L), of at least one organic solvent. Medium (L) preferably comprises at most 100 wt. %, more preferably at most 99 wt. % based on the total weight of said medium (L), of at least one organic solvent.

The medium (L) may further comprise at least one non-solvent medium [medium (NS)]. The medium (NS) may comprise water.

Under step (iˆ), composition ($C^L$) is manufactured by any conventional techniques. For instance, the medium (L) may be added to polymer (A) and the F-TPU polymer, or, preferably, polymer (A) and the F-TPU polymer are added to the medium (L), or even the polymer (A), the F-TPU polymer and the medium (L) are simultaneously mixed.

Any suitable mixing equipment may be used. Preferably, the mixing equipment is selected to reduce the amount of air entrapped in composition ($C^L$) which may cause defects in the final membrane. The mixing of polymer (A), the F-TPU polymer and the medium (L) may be conveniently carried out in a sealed container, optionally held under an inert atmosphere. Inert atmosphere, and more precisely nitrogen atmosphere has been found particularly advantageous for the manufacture of composition ($C^L$).

Under step (iˆ), the mixing time during stirring required to obtain a clear homogeneous composition ($C^L$) can vary widely depending upon the rate of dissolution of the components, the temperature, the efficiency of the mixing apparatus, the viscosity of composition ($C^L$) and the like.

Under step (iiˆ), composition ($C^L$) is typically processed in liquid phase.

Under step (iiˆ), composition ($C^L$) is typically processed by casting thereby providing a film.

Casting generally involves solution casting, wherein typically a casting knife, a draw-down bar or a slot die is used to spread an even film of a liquid composition comprising a suitable medium (L) across a suitable support.

Under step (iiˆ), the temperature at which composition ($C^L$) is processed by casting may be or may be not the same as the temperature at which composition ($C^L$) is mixed under stirring.

Different casting techniques are used depending on the final form of the membrane to be manufactured.

When the final product is a flat membrane, composition ($C^L$) is cast as a film over a flat supporting substrate, typically a plate, a belt or a fabric, or another microporous supporting membrane, typically by means of a casting knife, a draw-down bar or a slot die.

According to a first embodiment of step (iiˆ), composition ($C^L$) is processed by casting onto a flat supporting substrate to provide a flat film.

According to a second embodiment of step (iiˆ), composition ($C^L$) is processed by casting to provide a tubular film.

According to a variant of this second embodiment of the invention, the tubular film is manufactured using a spinneret.

The term "spinneret" is hereby understood to mean an annular nozzle comprising at least two concentric capillaries: a first outer capillary for the passage of composition ($C^L$) and a second inner one for the passage of a supporting fluid, generally referred to as "lumen". Optionally an external outer capillary can be used to extrude a coating layer.

Hollow fibers and capillary membranes may be manufactured by the so-called spinning process according to this variant of the second embodiment of step (iiˆ). According to this variant of the second embodiment of the invention, composition ($C^L$) is generally pumped through the spinneret. The lumen acts as the support for the casting of the composition ($C^L$) and maintains the bore of the hollow fiber or capillary precursor open. The lumen may be a gas, or, preferably, a medium (NS) or a mixture of the medium (NS) with a medium (L). The selection of the lumen and its temperature depends on the required characteristics of the final membrane as they may have a significant effect on the size and distribution of the pores in the membrane.

At the exit of the spinneret, after a short residence time in air or in a controlled atmosphere, under step (iiiˆ) of the process for manufacturing a porous membrane according to this first embodiment of the invention, the hollow fiber or capillary precursor is precipitated thereby providing the hollow fiber or capillary membrane.

The supporting fluid forms the bore of the final hollow fiber or capillary membrane.

Tubular membranes, because of their larger diameter, are generally manufactured using a different process from the one employed for the production of hollow fiber membranes.

The Applicant has found that use of solvent/non-solvent mixtures in any one of steps (iiˆ) and (iiiˆ) of the process of the invention, at a given temperature advantageously allows controlling the morphology of the final porous membrane including its average porosity.

The temperature gradient between the film provided in any one of steps (iiˆ) and (iiiˆ) of the process for manufacturing a porous membrane according to the first embodiment of the invention and the medium (NS) may also influence the pore size and/or pore distribution in the final porous membrane as it generally affects the rate of precipitation of the polymer (A) from composition ($C^L$).

According to a first variant of the first embodiment of the invention, the process for manufacturing a porous membrane comprises:

(iˆ*) providing a liquid composition [composition ($C^L$)] comprising:
  at least one polymer (A),
  at least one F-TPU polymer, and
  a liquid medium comprising at least one organic solvent [medium (L)];
(iiˆ*) processing composition ($C^L$) provided in step (iˆ*) thereby providing a film; and optionally
(iiiˆ*) precipitating the film provided in step (iiˆ*) in a non-solvent medium [medium (NS)] thereby providing a porous membrane.

Under step (iˆ*), the medium (L) typically further comprises water.

Under step pin, the medium (NS) typically comprises water and, optionally, at least one organic solvent.

According to a second variant of the first embodiment of the invention, the process for manufacturing a porous membrane comprises:

(iˆ**) providing a liquid composition [composition ($C^L$)] comprising:
  at least one polymer (A),
  at least one F-TPU polymer, and
  a liquid medium comprising at least one organic solvent [medium (L)];
(iiˆ) processing composition ($C^L$) provided in step (iˆ) thereby providing a film; and optionally
(iiiˆ) precipitating the film provided in step (iiˆ) by cooling thereby providing a porous membrane.

Under step (iˆ**), the medium (L) of composition ($C^L$) advantageously comprises at least one latent organic solvent.

For the purpose of the present invention, the term "latent" is intended to denote an organic solvent which behaves as an active solvent only when heated above a certain temperature.

Under step (ii^**), the film is typically processed at a temperature high enough to maintain composition ($C^L$) as a homogeneous solution.

Under step (ii^**), the film is typically processed at a temperature comprised between 60° C. and 250° C., preferably between 70° C. and 220°, more preferably between 80° C. and 200° C.

Under step (iii^), the film provided in step (ii^) is typically precipitated by cooling to a temperature below 100° C., preferably below 60° C., more preferably below 40° C., typically using any conventional techniques.

Under step (iii^**), cooling is typically carried out by contacting the film provided in step (ii) with a liquid medium [medium (L')].

Under step (iii^**), the medium (L') preferably comprises, and more preferably consists of, water.

Alternatively, under step (iii^), cooling is carried out by contacting the film provided in step (ii^) with air.

Under step (iii^**), either the medium (L') or air is typically maintained at a temperature below 100° C., preferably below 60° C., more preferably below 40° C.

According to a third variant of the first embodiment of the invention, the process for manufacturing a porous membrane comprises:
(i^') providing a liquid composition [composition ($C^L$)] comprising:
  at least one polymer (A),
  at least one F-TPU polymer, and
  a liquid medium comprising at least one organic solvent [medium (L)];
(ii^***) processing composition ($C^L$) provided in step (i^') thereby providing a film; and optionally
(iii^*) precipitating the film provided in step (ii^*) by absorption of a non-solvent medium [medium (NS)] from a vapour phase thereby providing a porous membrane.

Under step (iii^*), the film provided in step (ii^*) is preferably precipitated by absorption of water from a water vapour phase.

Under step (iii^*), the film provided in step (ii^*) is preferably precipitated under air, typically having a relative humidity higher than 10%, preferably higher than 50%.

According to a fourth variant of the first embodiment of the invention, the process for manufacturing a porous membrane comprises:
(i^****) providing a liquid composition [composition ($C^L$)] comprising:
  at least one polymer (A),
  at least one F-TPU polymer, and
  a liquid medium comprising at least one organic solvent [medium (L)];
(ii^**) processing composition ($C^L$) provided in step (i^**) thereby providing a film; and optionally
(iii^**) precipitating the film provided in step (ii^**) by evaporation of the medium (L) thereby providing a porous membrane.

Preferably, when the medium (L) comprise more than one organic solvents, step (ii^**) comprises processing composition ($C^L$) to provide a film, which is then precipitated in step (iii^**) by evaporation of the medium (L) at a temperature above the boiling point of the organic solvent having the lowest boiling point.

According to a preferred embodiment, step (ii^****) is performed by processing composition ($C^L$) with a high voltage electric field.

For the purpose of the present invention, by the term "non-solvent medium [medium (NS)]" it is meant a medium consisting of one or more liquid substances incapable of dissolving the composition (C) at a given temperature.

The medium (NS) typically comprises water and, optionally, at least one organic solvent selected from alcohols or polyalcohols, preferably aliphatic alcohols having a short chain, for example from 1 to 6 carbon atoms, more preferably methanol, ethanol, isopropanol and ethylene glycol.

The medium (NS) is generally selected among those miscible with the medium (L) used for the preparation of composition ($C^L$).

The medium (NS) may further comprise the medium (L).

More preferably, the medium (NS) consists of water. Water is the most inexpensive non-solvent medium and can be used in large amounts.

The medium (L) is advantageously soluble in water, which is an additional advantage of the process of the present invention.

The process for manufacturing the film or the porous membrane according to the first embodiment may comprise any combination of the first, second, third and fourth variants as defined above. For instance, the film or the porous membrane according to the present invention may be obtainable by the process according to the second variant of the first embodiment of the invention followed by the process according to the first variant of the first embodiment of the invention.

The porous membrane obtainable by the process according to the first embodiment may undergo additional post treatment steps, for instance rinsing and/or stretching.

The porous membrane obtainable by the process according to the first embodiment of the invention is typically rinsed using a liquid medium miscible with the medium (L).

The porous membrane obtainable by the process according to the first embodiment of the invention may be advantageously stretched so as to increase its average porosity.

According to a second embodiment of the invention, the process for manufacturing a porous membrane is carried out in molten phase.

The process according to the second embodiment of the invention preferably comprises the following steps:
(i^^) providing a solid composition [composition ($C^S$)] comprising:
  at least one polymer (A), and
  at least one F-TPU polymer;
(ii^^-A) processing the composition ($C^S$) provided in step (i^-A) thereby providing a film and,
optionally (iii^^-A) stretching the film provided in step (ii^^-A); or
(ii^^-B) processing the composition ($C^S$) provided in step (i^^) thereby providing fibers and,
optionally (iii^^-B) processing the fibers provided in (ii^^-B) thereby providing a membrane.

Under step (ii^^-A), composition ($C^S$) is preferably processed in molten phase.

Melt forming is commonly used to make dense films by film extrusion, preferably by flat cast film extrusion or by blown film extrusion.

According to this technique, composition ($C^S$) is extruded through a die so as to obtain a molten tape, which is then calibrated and stretched in the two directions until obtaining the required thickness and wideness. Composition ($C^S$) is melt compounded for obtaining a molten composition. Generally, melt compounding is carried out in an extruder. Composition ($C^S$) is typically extruded through a die at temperatures of generally lower than 250° C., preferably lower than 200° C. thereby providing strands which are typically cut thereby providing pellets.

Twin screw extruders are preferred devices for accomplishing melt compounding of composition ($C^S$).

Films can then be manufactured by processing the pellets so obtained through traditional film extrusion techniques. Film extrusion is preferably accomplished through a flat cast film extrusion process or a hot blown film extrusion process. Film extrusion is more preferably accomplished by a hot blown film extrusion process.

Under step (iii^^-A), the film provided in step (ii^^-A) may be stretched either in molten phase or after its solidification upon cooling.

Under step (iii^^-A), the film provided in step (ii^^-A) is advantageously stretched at right angle to the original orientation, so that the crystalline structure of the polymer (A) is typically deformed and slit-like voids are advantageously formed.

The porous membrane obtainable by the process of the invention is typically dried, preferably at a temperature of at least 30° C.

Drying can be performed under air or a modified atmosphere, e.g. under an inert gas, typically exempt from moisture (water vapour content of less than 0.001% v/v). Drying can alternatively be performed under vacuum.

The porous membrane of the invention may be in the form of flat membranes or in the form of tubular membranes.

Flat membranes are generally preferred when high fluxes are required whereas hollow fibers membranes are particularly advantageous in applications wherein compact modules having high surface areas are required.

Flat membranes preferably have a thickness comprised between 10 μm and 200 μm, more preferably between 15 μm and 150 μm.

Tubular membranes typically have an outer diameter greater than 3 mm. Tubular membranes having an outer diameter comprised between 0.5 mm and 3 mm are typically referred to as hollow fibers membranes. Tubular membranes having a diameter of less than 0.5 mm are typically referred to as capillary membranes.

According to a preferred embodiment, composition (C) is free of plasticizer agents, i.e. plasticizer agents are not added to composition (C) or they are present in an amount of less than 1 wt. %, more preferably less than 0.1 wt. % based on the total weight of said composition (C).

Preferably, composition (C) comprises said polymer (A) in an amount of from 10 to 100 wt. % based on the total weight of said composition (C).

Preferably, composition (C) comprises said F-TPU polymer in an amount of from 0.1 to 80 wt. % based on the total weight of said composition (C).

Preferably, composition (C) comprises at least one further ingredient, more preferably said at least one further ingredient is in an amount of from 0.1 to 30 wt. % based on the total weight of said composition (C).

Said optional at least one further ingredient is preferably selected in the group comprising: polar aprotic solvents [medium (L)] as defined above, pore forming agents, nucleating agents, fillers, salts, latent organic solvents, surfactants.

Pore forming agents are typically added to the composition (C) in amounts usually ranging from 0.1% to 30% by weight, preferably from 0.5% to 5% by weight. Suitable pore forming agents are for instance polyvinyl-pyrrolidone (PVP) and polyethyleneglycol (PEG), with PVP being preferred.

Pore forming agents are generally at least partially, if not completely, removed from the porous membrane in the medium (NS), if any, under step (iii) of the process for manufacturing a porous membrane according to the first embodiment of the invention.

Composition (C) according to the present invention can be in the form of a liquid composition [composition ($C^L$)] or in the form of a solid composition [composition ($C^S$)].

Composition ($C^L$) preferably comprises at least one F-TPU polymer in an amount of at least 1 wt. %, more preferably of at least 5 wt. %, based on the total weight of said composition ($C^L$).

Composition ($C^L$) preferably comprises at least one F-TPU polymer in an amount of at most 80 wt. %, more preferably of at most 75 wt. %, based on the total weight of said composition ($C^L$).

Even more preferably, composition ($C^L$) comprises at least one F-TPU polymer in an amount from 5 to 70 wt. % based on the total weight of said composition ($C^L$).

Composition ($C^L$) preferably comprises at least one polymer (A) in an amount of at least 10 wt. %, more preferably of at least 15 wt. %, based on the total weight of said composition ($C^L$).

Composition ($C^L$) preferably comprises at least one polymer (A) in an amount of at most 100 wt. %, more preferably of at most 90 wt. %, based on the total weight of said composition ($C^L$).

Even more preferably, composition ($C^L$) comprises at least one polymer (A) in an amount from 10 to 70 wt. % based on the total weight of said composition ($C^L$).

Composition ($C^L$) preferably comprises at least one medium (L) in an amount of at least 5 wt. %, more preferably of at least 7 wt. % based on the total weight of said composition ($C^L$).

Composition ($C^L$) preferably comprises at least one medium (L) in an amount of at most 95 wt. %, more preferably of at most 90 wt. % based on the total weight of said composition ($C^L$).

Even more preferably, composition ($C^L$) comprises at least one medium (L) in an amount from 20 to 90 wt. % based on the total weight of said composition ($C^L$).

Further, in addition, a limited amount of a medium (NS) for the F-TPU polymer may be added to composition ($C^L$), in an amount generally below the level required to reach the cloud point, typically in amount of from 0.1% to 40% by weight, preferably in amount of from 0.1% to 20% by weight, based on the total weight of composition ($C^L$).

Without being bound by this theory, it is generally understood that the addition of a medium (NS) to composition ($C^L$) will increase the rate of demixing/coagulation under step (iii) of the process for manufacturing a porous membrane according to the first embodiment of the invention thereby providing a more advantageous membrane morphology.

Composition ($C^L$) can optionally comprise at least one further ingredient, selected from those disclosed above for composition (C), in the same amounts.

Composition ($C^S$) preferably comprises at least one polymer (A) in an amount of at least 50% by weight, preferably of at least 65% by weight, based on the total weight of composition ($C^S$).

Composition ($C^S$) preferably comprises at least one polymer (A) in an amount of at most 99% by weight, preferably of at most 95% by weight, based on the total weight of composition ($C^S$).

Even more preferably, composition ($C^S$) comprises at least one polymer (A) in an amount from 70 to 97 wt. % based on the total weight of said composition ($C^S$).

Composition ($C^S$) preferably comprises at least one F-TPU polymer in an amount of at least 1% by weight, preferably of at least 5% by weight, based on the total weight of composition ($C^S$).

Composition ($C^S$) preferably comprises at least one polymer (A) in an amount of at most 50% by weight, preferably of at most 35% by weight, based on the total weight of composition ($C^S$).

Even more preferably, composition ($C^S$) comprises at least one polymer (A) in an amount from 3 to 30 wt. % based on the total weight of said composition ($C^S$).

The dense film and the porous membrane according to the present invention can be used in several technical fields, notably for the filtration of liquid and/or gas phases or it is embedded or laminated into a multi-layered fabric, in order to provide the so-called 'breathable fabric'.

Thus, in a sixth aspect, the present invention pertains to use of the porous membrane of the invention for the filtration of liquid and/or gas phases comprising one or more solid contaminants.

In a seventh aspect, the present invention relates to a method for filtering a liquid phase and/or a gas phase comprising one or more solid contaminants, said method comprising contacting said liquid phase and/or gas phase comprising one or more solid contaminants with the porous membrane of the invention.

Liquid and gas phases comprising one or more solid contaminants are also referred to as "suspensions", i.e. heterogeneous mixtures comprising at least one solid particle (the contaminant) dispersed into a continuous phase (or "dispersion medium", which is in the form of liquid or gas).

Said at least one solid contaminant preferably comprises comprising microorganisms, preferably selected from the group consisting of bacteria such as *Staphylococcus aureus* and *Pseudomonas aeruginosa*, algae, fungi, protozoa and viruses.

The porous membrane according to the present invention can be used for filtrating biologic solution (e.g. bioburden, virus, other large molecules) and/or buffer solutions (e.g. solutions that may contain small amount of solvents like DMSO or other polar aprotic solvents).

In one embodiment, two or more porous membranes according to the present invention can be used in series for the filtration of a liquid and/or gas phase. Advantageously, a first filtration step is performed by contacting liquid and/or gas phases comprising one or more solid contaminants with a porous membrane according to the present invention having an average pore diameter higher than 5 µm, more preferably from 5 to 50 µm; and a second filtration step is performed after said first filtration step, by contacting the same liquid and/or gas phase with a porous membrane according to the present invention having an average pore diameter of from 0.001 to 5 µm.

Alternatively, at least one porous membrane according to the present invention is used in series with at least one porous membrane obtained from a composition different composition (C) according to the present invention.

According to a specific embodiment and in an eight aspect of the invention, porous membranes according to the present invention in the form of tubular or hollow fiber and having average pore diameter of from 0.001 to 5 µm are used within an extracorporeal blood circuit or a dialysis filter to purify biological fluids, such as notably blood.

Without being bound by any theory, the Applicant believes that porous membranes according to the present invention are antithrombogenic when contacted with blood due to the water- and oleo-repellency properties provided by the F-TPU polymer to the surface of the membranes.

As used within the present invention, the term "antithrombogenic" is intended to indicate that the rate at which thrombosis occurs upon exposure to whole blood is reduced in the porous membrane according to the present invention when compared to a membrane prepared starting from a composition free from the at least one F-TPU polymer defined above. It is well known in the art, for example from US 2015/0008179 (INTERFACE BIOLOGICS INC.) that when blood is transported to and from the body of patients receiving haemodialysis, anticoagulants such as heparin are typically added to prevent clotting or thrombosis. However, if on the one hand the use of heparin is advantageous, it can be complicated by allergic reactions and bleeding and, in addition, it is contraindicated in patients taking certain medications.

Thus, in a ninth aspect, the present invention relates to the use of a hollow fiber membrane having an average pore diameter of from 0.001 to 5 µm as component in an extracorporeal blood circuit or in a dialysis filter.

In an tenth aspect, the present invention relates to a method for treating a subject suffering from impaired kidney function, wherein the method includes performing a procedure selected from haemodialysis, hemofiltration, hemoconcentration or hemodiafiltration on a patient using a dialysis filter, wherein said filter comprises at least one porous membrane according to the invention in the form of tubular or hollow fiber having an average pore diameter of from 0.001 to 5 µm.

In a eleventh aspect, the present invention relates to a method for purifying a blood product, such as whole blood, plasma, fractionated blood component or mixtures thereof, wherein the method includes dialyzing said blood product across at least one hollow fiber membrane having an average pore diameter of from 0.001 to 5 µm and comprising at least one layer consisting of a composition [composition (C)] as defined above.

Then in a twelfth aspect, the present invention relates to a fabric comprising at least two layers, wherein at least one layer comprises a porous membrane according to the present invention having an average pore diameter of from 0.001 to 5 µm and/or wherein at least one layer comprises at least one dense film according to the present invention.

Breathable fabrics are typically designed for use in garments that provide protection from wind, rain and loss of body heat. Breathable fabrics are typically also waterproof (and hence referred to as waterproof breathable fabrics, WBF), in order to prevent the penetration and absorption of liquid water. The term "breathable" is intended to indicate that the fabric passively allows water vapour due to perspiration from the body to diffuse through the fabric, yet still preventing the penetration of liquid water from the outside.

Without being bound by any theory, the Applicant believes that the layer made from the porous membrane according to the present invention provides a breathable layer, i.e. a layer that allows the water vapour produced from the perspiration of the body to diffuse outside the fabric, while preventing penetration of the liquid water from the outside (for example the rain).

Without being bound by any theory, the Applicant believes that the layer made from the dense film according to the present invention provides a support layer that still allows the water vapour produced from the perspiration of the body to diffuse outside the fabric, while providing on the one hand a hydrophobic layer against the penetration of liquid water from the outside and on the other hand mechanical support to the fabric.

WBFs are typically manufactured as continuous rolls of 1.5 to 2 meters wide and 100 to 5000 meters long. WBFs can be manufactured for example as follows:

providing a substrate, such as for example woven substrates or polymeric substrates;

contacting said substrate with composition (C) as defined above;

optionally, transfer coating; and lamination.

The dense film according to the present invention is also advantageously used for the manufacture of tubes, notably for use in medicine, such as for example catheters and implantable devices.

Thus, in a further aspect the present invention relates to a catheter comprising at least one layer made from the dense film according to the present invention.

Should the disclosure of any patents, patent applications, and publications which are incorporated herein by reference conflict with the description of the present application to the extent that it may render a term unclear, the present description shall take precedence.

The invention will be herein after illustrated in greater detail by means of the Examples contained in the following Experimental Section; the Examples are merely illustrative and are by no means to be interpreted as limiting the scope of the invention.

Experimental Section

Materials:

Solvents and additives were obtained from Sigma Aldrich:

dimethylacetamide (DMAc), triethylphospate (TEP), polyethilenglycol (PEG) 200 and isopropyl alcohol (IPA).

Polysulfone (PSU) UDEL® 3500 MB3 and Polyethersulfone (PES) VERADEL 3000 MP were obtained from Solvay Specialty Polymers.

Monomer (a):

CAPA™ 2201 (from Perstorp) polycaprolactone-diol (PLC) having molecular weight ($M_w$) of about 2,000 and —OH value of about 56 mg KOH/g;

Monomer (b) having formula:

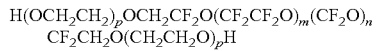

H(OCH$_2$CH$_2$)$_p$OCH$_2$CF$_2$O(CF$_2$CF$_2$O)$_m$(CF$_2$O)$_n$CF$_2$CH$_2$O(CH$_2$CH$_2$O)$_p$H having p=4.7 and $M_w$ of about 2,000

Monomer (c):

diphenylen-4,4'-diisocyanate (MDI)

Monomer (d):

1,4-butanediol (BDO)

Catalyst:

zinc neodecanoate

Solvents and additives were obtained from Sigma Aldrich:

dimethylacetamide (DMAc) and triethylphosphate (TEP) polyethylene glycol (PEG) 200, isopropyl alcohol (IPA)

Methods

Preparation of F-TPU Polymer Specimens

F-TPU polymer specimens 1 to 3 were prepared starting from the abovementioned monomers following the same procedure detailed in Example 15 of U.S. Pat. No. 5,332,798 (to Ausimont S.p.A.) cited above. The monomers were used in the molar ratios reported in the following Table 1.

TABLE 1

| | Monomers (molar ratio) | | | |
|---|---|---|---|---|
| | a | b | c | d |
| F-TPU 1 | 0.75 | 0.25 | 3.0 | 2.0 |
| F-TPU 2 | 0.86 | 0.14 | 3.0 | 2.0 |
| F-TPU 3 | 0.29 | 0.71 | 3.0 | 2.0 |

Solution Preparation

Solutions were prepared by adding each polymer and the additive in the solvent DMAC or TEP. After mixing, stirring was performed with a mechanical anchor for 4 hours at 60° C.

Porous Membrane Preparation

Flat sheet porous membranes were prepared by filming the solution prepared following the procedure disclosed above over a smooth glass support by means of an automatized casting knife.

Membrane casting was performed by holding dope solutions, the casting knife and the support temperatures at 25° C., so as to prevent premature precipitation of the polymer. The knife gap was set to 250 μm. After casting, polymeric films were immediately immersed in a coagulation bath in order to induce phase inversion. The coagulation bath consisted of pure de-ionized water or a mixture isopropyl alcohol (IPA)/water 50/50 v/v. After coagulation the membranes were washed several times in pure water during the following days to remove residual traces of solvent. The membranes were always stored (wet) in water.

Measurement of Contact Angle (CA)

The contact angle towards water and hexadecane (C16) was evaluated at 25° C. by using the DSA10 instrument (from Krüss GmbH, Germany) according to ASTM D5725-99. The measures were taken at the up side (interface with air) of the membrane.

Mechanical Properties

Mechanical properties on flat sheet porous membranes were assessed at room temperature (23° C.) following ASTM D 638 standard procedure (type V, grip distance=25.4 mm, initial length Lo=21.5 mm). Velocity was between 1 and 50 mm/min. The flat sheet porous membranes stored in water were took out from the container boxes and immediately tested.

The properties of each membrane are summarized in the following Tables 2 and 3.

TABLE 2

| Membrane No. | Ingredient(s) | Amount (wt. %) | Solvent | Coagulation bath | SCA water (°) | SCA C16 (°) |
|---|---|---|---|---|---|---|
| 1(*) | PSU | 25 | DMAc | water | 76 | wet |
| 2 | F-TPU 1 | 3 | DMAc | water | 99 | 54 |
| | PSU | 22 | | | | |
| 3 | F-TPU 2 | 3 | DMAc | water | 89 | 43 |
| | PSU | 22 | | | | |
| 4 | F-TPU 3 | 3 | DMAc | water | 111 | 62 |
| | PSU | 22 | | | | |
| 5 | F-TPU 2 | 3 | DMAc | water | 92 | 49 |
| | PES | 22 | | | | |
| 6 | F-TPU 2 | 3 | DMAc | water | 85 | 48 |
| | PES | 22 | | | | |
| 7(*) | PES | 25 | DMAc | water | 79 | wet |

(*)comparison

The above results show that the porous membranes according to the present invention are both highly hydrophobic and highly oleophobic. On the other hand, the porous membranes obtained with the aromatic polymers only are less hydrophobic that the porous membranes according to the present invention and are not oleophobic, i.e. the drop of hexadecane penetrates into the membrane ("wet" in Table 2).

TABLE 3

| Membrane No. | Stress at break (MPa) | Strain at break (%) |
|---|---|---|
| 1(*) | 7.7 | 16.9 |
| 2 | 9.7 | 38 |
| 5 | 10.5 | 60.1 |
| 7(*) | 9.8 | 25.8 |

(*)comparison

The above results show that the porous membranes according to the present invention have better mechanical properties when compared to the porous membranes obtained from the aromatic polymer only.

The invention claimed is:

1. A composition (C) comprising:
   at least one aromatic polymer (A);
   at least one F-TPU polymer, wherein said F-TPU polymer is a fluorinated polyurethane polymer comprising recurring units derived from:
   optionally, at least one monomer (a), wherein monomer (a) is a diol selected from the group consisting of poly-ether type diols, poly-ester type diols, polybutadien-diols and polycarbonate-diols;
   at least one monomer (b), wherein monomer (b) is a hydroxy-terminated (per)fluoropolyether polymer comprising a chain ($R_{pf}$);
      wherein said chain ($R_{pf}$) is a chain of formula —O-D-$(CFX^\#)_{z1}$—O$(R_f)(CFX^*)_{z2}$-D*-O—;
      wherein z1 and z2, equal or different from each other, are equal to or higher than 1;
      wherein $X^\#$ and $X^*$, equal or different from each other, are —F or —$CF_3$, provided that when z1 and/or z2 are higher than 1, $X^\#$ and $X^*$ are —F;
      wherein D and D*, equal or different from each other, are an alkylene chain comprising from 1 to 6 carbon atoms, said alkylene chain being optionally substituted with at least one perfluoroalkyl group comprising from 1 to 3 carbon atoms; and
      wherein ($R_f$) comprises repeating units $R^\circ$, said repeating units being independently selected from the group consisting of:
         (i) —CFXO—, wherein X is F or $CF_3$;
         (ii) —CFXCFXO—, wherein X, equal or different at each occurrence, is F or $CF_3$, with the proviso that at least one of X is —F;
         (iii) —$CF_2CF_2CW_2O$—, wherein each of W, equal or different from each other, is F, Cl, H;
         (iv) —$CF_2CF_2CF_2CF_2O$—; and
         (v) —$(CF_2)_j$—CFZ—O— wherein j is an integer from 0 to 3 and Z is a group of general formula —O—$R_{(f-a)}$-T, wherein $R_{(f-a)}$ is a fluoropolyoxyalkene chain comprising a number of repeating units from 0 to 10, said recurring units being chosen among the following: —CFXO—, —$CF_2CFXO$—, —$CF_2CF_2CF_2O$—, —$CF_2CF_2CF_2CF_2O$—, with each of each of X being independently F or $CF_3$ and T being a $C_1$-$C_3$ perfluoroalkyl group;
   at least one monomer (c), wherein monomer (c) is an aromatic, aliphatic or cycloaliphatic diisocyanate; and
   at least one monomer (d), wherein monomer (d) is an aliphatic, cycloaliphatic or aromatic diol having from 1 to 14 carbon atoms; and
   optionally at least one further ingredient.

2. A film comprising at least one layer obtained from a composition (C), wherein composition (C) comprises:
   at least one aromatic polymer (A);
   at least one F-TPU polymer, wherein said F-TPU polymer is a fluorinated polyurethane polymer comprising recurring units derived from:
   optionally at least one monomer (a), wherein monomer (a) is a diol selected from the group consisting of poly-ether type diols, poly-ester type diols, polybutadien-diols and polycarbonate-diols;
   at least one monomer (b), wherein monomer (b) is a hydroxy-terminated (per)fluoropolyether polymer comprising a chain ($R_{pf}$);
      wherein said chain ($R_{pf}$) is a chain of formula —O-D-$(CFX^\#)_{z1}$—O$(R_f)(CFX^*)_{z2}$-D*-O—;
      wherein z1 and z2, equal or different from each other, are equal to or higher than 1;
      wherein $X^\#$ and $X^*$, equal or different from each other, are —F or —$CF_3$, provided that when z1 and/or z2 are higher than 1, $X^\#$ and $X^*$ are —F;
      wherein D and D*, equal or different from each other, are an alkylene chain comprising from 1 to 6 carbon atoms, said alkylene chain being optionally substituted with at least one perfluoroalkyl group comprising from 1 to 3 carbon atoms; and
      wherein ($R_f$) comprises repeating units $R^\circ$, said repeating units being independently selected from the group consisting of:
         (i) —CFXO—, wherein X is F or $CF_3$;
         (ii) —CFXCFXO—, wherein X, equal or different at each occurrence, is F or $CF_3$, with the proviso that at least one of X is —F;
         (iii) —$CF_2CF_2CW_2O$—, wherein each of W, equal or different from each other, is F, Cl, H;
         (iv) —$CF_2CF_2CF_2CF_2O$—; and
         (v) —$(CF_2)_j$—CFZ—O— wherein j is an integer from 0 to 3 and Z is a group of general formula —O—$R_{(f-a)}$-T, wherein $R_{(f-a)}$ is a fluoropolyoxyalkene chain comprising a number of repeating units from 0 to 10, said recurring units being chosen among the following: —CFXO—, —$CF_2CFXO$—, —$CF_2CF_2CF_2O$—, —$CF_2CF_2CF_2CF_2O$—, with each of each of X being independently F or $CF_3$ and T being a $C_1$-$C_3$ perfluoroalkyl group;
   at least one monomer (c), wherein monomer (c) is an aromatic, aliphatic or cycloaliphatic diisocyanate; and
   at least one monomer (d), wherein monomer (d) is an aliphatic, cycloaliphatic or aromatic diol having from 1 to 14 carbon atoms; and
   optionally at least one further ingredient.

3. The film according to claim 2, wherein said film is a dense film.

4. A porous membrane comprising at least one layer obtained from a composition (C) comprising:
   at least one aromatic polymer (A);
   at least one F-TPU polymer, wherein said F-TPU polymer is a fluorinated polyurethane polymer comprising recurring units derived from:

optionally at least one monomer (a), wherein monomer (a) is a diol selected from the group consisting of poly-ether type diols, poly-ester type diols, polybutadien-diols and polycarbonate-diols;

at least one monomer (b), wherein monomer (b) is a hydroxy-terminated (per)fluoropolyether polymer comprising a chain ($R_{pf}$);

wherein said chain ($R_{pf}$) is a chain of formula —O-D-$(CFX^\#)_{z1}$—O$(R_f)(CFX^*)_{z2}$-D*-O—;

wherein z1 and z2, equal or different from each other, are equal to or higher than 1;

wherein $X^\#$ and $X^*$, equal or different from each other, are —F or —$CF_3$, provided that when z1 and/or z2 are higher than 1, $X^\#$ and $X^*$ are —F;

wherein D and D*, equal or different from each other, are an alkylene chain comprising from 1 to 6 carbon atoms, said alkylene chain being optionally substituted with at least one perfluoroalkyl group comprising from 1 to 3 carbon atoms; and wherein ($R_f$) comprises repeating units R°, said repeating units being independently selected from the group consisting of:
(i) —CFXO—, wherein X is F or $CF_3$;
(ii) —CFXCFXO—, wherein X, equal or different at each occurrence, is F or $CF_3$, with the proviso that at least one of X is —F;
(iii) —$CF_2CF_2CW_2O$—, wherein each of W, equal or different from each other, is F, Cl, H;
(iv) —$CF_2CF_2CF_2CF_2O$—; and
(v) —$(CF_2)_j$—CFZ—O— wherein j is an integer from 0 to 3 and Z is a group of general formula —O—$R_{(f-a)}$-T, wherein $R_{(f-a)}$ is a fluoropolyoxyalkene chain comprising a number of repeating units from 0 to 10, said recurring units being chosen among the following: —CFXO—, —$CF_2CFXO$—, —$CF_2CF_2CF_2O$—, —$CF_2CF_2CF_2CF_2O$—, with each of each of X being independently F or $CF_3$ and T being a $C_1$-$C_3$ perfluoroalkyl group;

at least one monomer (c), wherein monomer (c) is an aromatic, aliphatic or cycloaliphatic diisocyanate; and at least one monomer (d), wherein monomer (d) is an aliphatic, cycloaliphatic or aromatic diol having from 1 to 14 carbon atoms; and optionally at least one further ingredient.

5. The porous membrane according to claim 4, wherein said porous membrane is obtained from a film comprising at least one layer obtained from a composition (C), wherein composition (C) comprises:

at least one aromatic polymer (A);

at least one F-TPU polymer, wherein said F-TPU polymer is a fluorinated polyurethane polymer comprising recurring units derived from:

optionally at least one monomer (a), wherein monomer (a) is a diol selected from the group consisting of poly-ether type diols, poly-ester type diols, polybutadien-diols and polycarbonate-diols;

at least one monomer (b), wherein monomer (b) is a hydroxy-terminated (per)fluoropolyether polymer comprising a chain ($R_{pf}$);

wherein said chain ($R_{pf}$) is a chain of formula —O-D-$(CFX^\#)_{z1}$—O$(R_f)(CFX^*)_{z2}$-D*-O—;

wherein z1 and z2, equal or different from each other, are equal to or higher than 1;

wherein $X^\#$ and $X^*$, equal or different from each other, are —F or —$CF_3$, provided that when z1 and/or z2 are higher than 1, $X^\#$ and $X^*$ are —F;

wherein D and D*, equal or different from each other, are an alkylene chain comprising from 1 to 6 carbon atoms, said alkylene chain being optionally substituted with at least one perfluoroalkyl group comprising from 1 to 3 carbon atoms; and wherein ($R_f$) comprises repeating units R°, said repeating units being independently selected from the group consisting of:
(i) —CFXO—, wherein X is F or $CF_3$;
(ii) —CFXCFXO—, wherein X, equal or different at each occurrence, is F or $CF_3$, with the proviso that at least one of X is —F;
(iii) —$CF_2CF_2CW_2O$—, wherein each of W, equal or different from each other, is F, Cl, H;
(iv) —$CF_2CF_2CF_2CF_2O$—; and
(v) —$(CF_2)_j$—CFZ—O— wherein j is an integer from 0 to 3 and Z is a group of general formula —O—$R_{(f-a)}$-T, wherein $R_{(f-a)}$ is a fluoropolyoxyalkene chain comprising a number of repeating units from 0 to 10, said recurring units being chosen among the following: —CFXO—, —$CF_2CFXO$—, —$CF_2CF_2CF_2O$—, —$CF_2CF_2CF_2CF_2O$—, with each of each of X being independently F or $CF_3$ and T being a $C_1$-$C_3$ perfluoroalkyl group;

at least one monomer (c), wherein monomer (c) is an aromatic, aliphatic or cycloaliphatic diisocyanate; and at least one monomer (d), wherein monomer (d) is an aliphatic, cycloaliphatic or aromatic diol having from 1 to 14 carbon atoms; and optionally at least one further ingredient.

6. The porous membrane according to claim 4, wherein said porous membrane has an average pore diameter of from 0.001 to 5 μm.

7. The porous membrane according to claim 4, wherein said porous membrane is in the form of a tubular or hollow fiber.

8. A process for the manufacture of a film according to claim 2, said process comprising:

processing a composition (C) thereby providing a film, wherein composition (C) comprises:

at least one aromatic polymer (A), at least one F-TPU polymer, wherein said F-TPU polymer is a fluorinated polyurethane polymer comprising recurring units derived from:

optionally, at least one monomer (a), wherein monomer (a) is a diol selected from the group consisting of poly-ether type diols, poly-ester type diols, polybutadien-diols and polycarbonate-diols;

at least one monomer (b), wherein monomer (b) is a hydroxy-terminated (per)fluoropolyether polymer comprising a chain ($R_{pf}$);

wherein said chain ($R_{pf}$) is a chain of formula —O-D-$(CFX^\#)_{z1}$—O$(R_f)(CFX^*)_{z2}$-D*-O—;

wherein z1 and z2, equal or different from each other, are equal to or higher than 1;

wherein $X^\#$ and $X^*$, equal or different from each other, are —F or —$CF_3$, provided that when z1 and/or z2 are higher than 1, $X^\#$ and $X^*$ are —F;

wherein D and D*, equal or different from each other, are an alkylene chain comprising from 1 to 6 carbon atoms, said alkylene chain being optionally substituted with at least one perfluoroalkyl group comprising from 1 to 3 carbon atoms; and wherein ($R_f$) comprises repeating units $R^o$, said repeating units being independently selected from the group consisting of:
(i) —CFXO—, wherein X is F or $CF_3$;
(ii) —CFXCFXO—, wherein X, equal or different at each occurrence, is F or $CF_3$, with the proviso that at least one of X is —F;
(iii) —$CF_2CF_2CW_2O$—, wherein each of W, equal or different from each other, is F, Cl, H;
(iv) —$CF_2CF_2CF_2CF_2O$—; and
(v) —$(CF_2)_j$—CFZ—O— wherein j is an integer from 0 to 3 and Z is a group of general formula —O—$R_{(f-a)}$-T, wherein $R_{(f-a)}$ is a fluoropolyoxyalkene chain comprising a number of repeating units from 0 to 10, said recurring units being chosen among the following: —CFXO—, —$CF_2CFXO$—, —$CF_2CF_2CF_2O$—, —$CF_2CF_2CF_2CF_2O$—, with each of each of X being independently F or $CF_3$ and T being a $C_1$-$C_3$ perfluoroalkyl group;

at least one monomer (c), wherein monomer (c) is an aromatic, aliphatic or cycloaliphatic diisocyanate; and at least one monomer (d), wherein monomer (d) is an aliphatic, cycloaliphatic or aromatic diol having from 1 to 14 carbon atoms; and optionally at least one further ingredient.

9. A process for the manufacture of a porous membrane according to claim 4, said process comprising:

processing a composition (C) thereby providing a film; and processing the film thereby providing a porous membrane, wherein composition (C) comprises:
at least one aromatic polymer (A),
at least one F-TPU polymer, wherein said F-TPU polymer is a fluorinated polyurethane polymer comprising recurring units derived from:
optionally, at least one monomer (a), wherein monomer (a) is a diol selected from the group consisting of poly-ether type diols, poly-ester type diols, polybutadien-diols and polycarbonate-diols;
at least one monomer (b), wherein monomer (b) is a hydroxy-terminated (per)fluoropolyether polymer comprising a chain ($R_{pf}$);
wherein said chain ($R_{pf}$) is a chain of formula —O-D-$(CFX^\#)_{z1}$—O$(R_f)(CFX^*)_{z2}$-D*-O—;
wherein z1 and z2, equal or different from each other, are equal to or higher than 1;
wherein $X^\#$ and $X^*$, equal or different from each other, are —F or —$CF_3$, provided that when z1 and/or z2 are higher than 1, $X^\#$ and $X^*$ are —F;
wherein D and D*, equal or different from each other, are an alkylene chain comprising from 1 to 6 carbon atoms, said alkylene chain being optionally substituted with at least one perfluoroalkyl group comprising from 1 to 3 carbon atoms; and
wherein ($R_f$) comprises repeating units $R^o$, said repeating units being independently selected from the group consisting of:
(i) —CFXO—, wherein X is F or $CF_3$;
(ii) —CFXCFXO—, wherein X, equal or different at each occurrence, is F or $CF_3$, with the proviso that at least one of X is —F;
(iii) —$CF_2CF_2CW_2O$—, wherein each of W, equal or different from each other, is F, Cl, H;
(iv) —$CF_2CF_2CF_2CF_2O$—; and
(v) —$(CF_2)_j$—CFZ—O— wherein j is an integer from 0 to 3 and Z is a group of general formula —O—$R_{(f-a)}$-T, wherein $R_{(f-a)}$ is a fluoropolyoxyalkene chain comprising a number of repeating units from 0 to 10, said recurring units being chosen among the following: —CFXO—, —$CF_2CFXO$—, —$CF_2CF_2CF_2O$—, —$CF_2CF_2CF_2CF_2O$—, with each of each of X being independently F or $CF_3$ and T being a $C_1$-$C_3$ perfluoroalkyl group;

at least one monomer (c), wherein monomer (c) is an aromatic, aliphatic or cycloaliphatic diisocyanate; and at least one monomer (d), wherein monomer (d) is an aliphatic, cycloaliphatic or aromatic diol having from 1 to 14 carbon atoms; and optionally at least one further ingredient.

10. A method for filtering a liquid phase and/or a gas phase comprising one or more solid contaminants, said method comprising contacting said liquid phase and/or gas phase comprising one or more solid contaminants with at least one porous membrane as defined in claim 4.

11. An extracorporeal blood circuit or a dialysis filter comprising, as a component, at least one porous membrane as defined in claim 6.

12. A method for treating a subject suffering from impaired kidney function, wherein the method includes performing a procedure selected from haemodialysis, hemofiltration, hemoconcentration or hemodiafiltration on a patient using a dialysis filter, wherein said filter comprises at least one porous membrane as defined in claim 6.

13. A method for purifying a blood product, wherein the method includes dialyzing said blood product across at least one porous membrane as defined in claim 6.

14. A fabric comprising at least two layers, wherein at least one layer comprises at least one porous membrane as defined in claim 4.

15. A catheter comprising at least one layer made from a dense film as defined in claim 3.

16. An extracorporeal blood circuit or a dialysis filter comprising, as a component, at least one porous membrane as defined in claim 7.

17. A method for treating a subject suffering from impaired kidney function, wherein the method includes performing a procedure selected from haemodialysis, hemofiltration, hemoconcentration or hemodiafiltration on a patient using a dialysis filter, wherein said filter comprises at least one porous membrane as defined in claim 7.

18. A method for purifying a blood product, wherein the method includes dialyzing said blood product across at least one porous membrane as defined in claim 7.

19. A fabric comprising at least two layers, wherein at least one layer comprises at least one dense film as defined in claim 3.

20. The composition (C) of claim 1, wherein D and D*, equal or different from each other, are an alkylene chain comprising from 1 to 3 carbon atoms.

21. The composition (C) of claim 1, wherein ($R_f$) consists of repeating units $R^o$.

* * * * *